(12) United States Patent
Wu et al.

(10) Patent No.: US 12,318,779 B2
(45) Date of Patent: Jun. 3, 2025

(54) MICROFLUIDIC CHIP FOR SORTING LIVING CELLS

(71) Applicants: GUANGZHOU HYBRIBIO MEDICINE TECHNOLOGY LTD., Guangdong (CN); HYBRIBIO MEDTECH DEVICE CO., LTD, Guangdong (CN); GUANGDONG HYBRIBIO BIOTECH CO., LTD., Guangdong (CN)

(72) Inventors: Yongguang Wu, Guangdong (CN); Xiang Chen, Guangdong (CN); Yan Zheng, Guangdong (CN); Mengyu Liu, Guangdong (CN); Jianhang Xiao, Guangdong (CN); Longxu Xie, Guangdong (CN)

(73) Assignees: GUANGZHOU HYBRIBIO MEDICINE TECHNOLOGY LTD., Guangdong (CN); HYBRIBIO MEDTECH DEVICE CO., LTD, Guangdong (CN); GUANGDONG HYBRIBIO BIOTECH CO., LTD., Guangdong (CN)

( * ) Notice: Subject to any disclaimer, the term of this patent is extended or adjusted under 35 U.S.C. 154(b) by 0 days.

(21) Appl. No.: 18/717,425

(22) PCT Filed: Jan. 4, 2024

(86) PCT No.: PCT/CN2024/070505
§ 371 (c)(1),
(2) Date: Jun. 7, 2024

(87) PCT Pub. No.: WO2024/255215
PCT Pub. Date: Dec. 19, 2024

(65) Prior Publication Data
US 2024/0416343 A1 Dec. 19, 2024

(30) Foreign Application Priority Data

Jun. 13, 2023 (CN) .......................... 202310694083.8

(51) Int. Cl.
*B01L 3/00* (2006.01)
*C12M 3/06* (2006.01)

(52) U.S. Cl.
CPC ... *B01L 3/502746* (2013.01); *B01L 3/502753* (2013.01); *C12M 23/16* (2013.01);
(Continued)

(58) Field of Classification Search
None
See application file for complete search history.

(56) References Cited

U.S. PATENT DOCUMENTS 9,957,554 B1 * 5/2018 Wu ...................... C12Q 1/6837

FOREIGN PATENT DOCUMENTS

| CN | 214088461 | 8/2021 |
| CN | 114292741 | 4/2022 |

(Continued)

OTHER PUBLICATIONS

You et al., WO 2023092735 A1 and Translation of WO 2023092735 A1, Jun. 1, 2023. (Year: 2023).*
(Continued)

*Primary Examiner* — Lore R Jarrett
(74) *Attorney, Agent, or Firm* — JCIPRNET

(57) ABSTRACT

The present invention relates to a microfluidic chip for sorting living cells. A sample flow channel communicates with a liquid inlet end of a sorting flow channel. A gas inlet flow channel, a target flow channel and a non-target flow channel communicate with a liquid outlet end of the sorting flow channel. An included angle between the target flow channel and the sorting flow channel is from 100° to 130°,
(Continued)

and an included angle between the non-target flow channel and the sorting flow channel is from 100° to 140°. A distance between an intersection of an axis of the gas inlet flow channel and an axis of the sorting flow channel and an intersection of the sorting flow channel, the target flow channel and the non-target flow channel is from 0.02 mm to 0.05 mm.

10 Claims, 2 Drawing Sheets

(52) U.S. Cl.
CPC .................. *B01L 2200/0636* (2013.01); *B01L 2200/0647* (2013.01); *B01L 2400/0487* (2013.01)

(56) References Cited

FOREIGN PATENT DOCUMENTS

| | | |
|---|---|---|
| CN | 114471760 | 5/2022 |
| CN | 217140437 | 8/2022 |
| CN | 116445246 | 7/2023 |

OTHER PUBLICATIONS

Song et al., CN 107164212 A and Translation of 107164212 A, Sep. 15, 2017 (Year: 2017).*
"International Search Report (Form PCT/ISA/210) of PCT/CN2024/070505", mailed on Apr. 12, 2024, pp. 1-3.

* cited by examiner

MICROFLUIDIC CHIP FOR SORTING LIVING CELLS

CROSS-REFERENCE TO RELATED APPLICATION

This application is a 371 of international application of PCT application serial no. PCT/CN2024/070505, filed on Jan. 4, 2024, which claims the priority benefit of China application no. 202310694083.8, filed on Jun. 13, 2023. The entirety of each of the above mentioned patent applications is hereby incorporated by reference herein and made a part of this specification.

TECHNICAL FIELD

The present invention relates to the technical field of cell sorting, and in particular to a microfluidic chip for sorting living cells.

BACKGROUND

With more and more in-depth studies in the field of cells, people are learning more and more about cells. In the study of cells, cell sorting is crucial in the study of cell physiology and pathology. The main technical means of cell sorting currently available on the market is the use of a combination of a flow cytometer and a microfluidic chip to sort the target cells from the cell population. A piezoelectric, magnetic or pneumatic driving structure may be used in the cell sorting chip to drive cells to change their trajectories. Compared with the other driving structures, the pneumatic driving structure causes the least damage to cells. Therefore, when living cells need to be sorted out, a cell sorting chip based on a pneumatic driving structure is mostly selected to sort out the target cells. For example, in an existing sorting device for simultaneously detecting multiple fluorescence signals in cells, the microfluidic chip includes a detecting area, a sorting region, a gas inlet, a waste liquid pool and a target cell pool. The detecting area and the sorting region are connected through a first cell flow channel, the sorting region and the waste liquid pool are connected through a second cell flow channel, the gas inlet and the sorting region are connected through a gas flow channel, and the target cell pool and the sorting region are connected through a sorting flow channel. The first cell flow channel, the second cell flow channel, the gas flow channel and the sorting flow channel are arranged in a cross shape around the sorting region. In this solution, the target cells are blown to the sorting flow channel by injecting gas into the gas flow channel. The gas causes less damage to the target cells as it changes their paths. However, the area of the sorting region is too small in this solution. When the flow velocity of the cell suspension in the sorting flow channel is too high, the residence time of the target cells in the sorting region is too short, so that it is difficult to ensure that the gas flow in the gas channel can accurately blow the target cells into the sorting flow channel, causing a low accuracy of cell sorting.

SUMMARY

The present invention provides a microfluidic chip for sorting living cells, in order to solve the problems in the solutions in the prior art: the area of the sorting region of the microfluidic chip is too small; and thus, when the flow velocity of the cell suspension in the sorting flow channel is too high, the residence time of the target cells in the sorting region is too short, so that it is difficult to ensure that the gas flow in the gas channel can accurately blow the target cells into the sorting flow channel, causing a low accuracy of cell sorting. In this solution, the area of the sorting region can be further increased so as to extend the residence time of cells in the sorting region, so that target cells can be accurately blown into the target flow channel by a gas flow, thereby increasing an accuracy of cell sorting.

The present invention adopts the following technical solution: A microfluidic chip for sorting living cells includes a sample region, a sample flow channel communicating with the sample region, an electromagnetic gas inlet valve, a gas inlet flow channel communicating with the electromagnetic gas inlet valve, a target cell pool, a target flow channel communicating with the target cell pool, a non-target cell pool, a non-target flow channel communicating with the non-target cell pool, and a sorting flow channel. The sample flow channel communicates with a liquid inlet end of the sorting flow channel, the target flow channel and the non-target flow channel communicate with a liquid outlet end of the sorting flow channel, and the gas inlet flow channel communicates with the sorting flow channel and is located on the sorting flow channel close to the liquid outlet end of the sorting flow channel. The gas inlet flow channel and the non-target flow channel are located on the other side of the sorting flow channel. An included angle between the target flow channel and the sorting flow channel is from 100° to 130°. An included angle between the non-target flow channel and the sorting flow channel is from 100° to 140°. An axis of the gas inlet flow channel is perpendicular to an axis of the sorting flow channel. A distance d between an intersection of the axis of the gas inlet flow channel and the axis of the sorting flow channel and an intersection of the sorting flow channel, the target flow channel and the non-target flow channel is from 0.02 mm to 0.05 mm. The cell sorting region is at an end of the sorting flow channel that intersects with the target flow channel, the non-target flow channel and the gas inlet flow channel.

When the microfluidic chip is running, target cells and non-target cells in the sample region enter the sample flow channel with the flow of a cell suspension and are arranged individually and linearly in the sample flow channel. As the cell suspension continuously flows forward, the target cells and the non-target cells enter the sorting flow channel. A device for identifying cell target signals identifies the cells which are entering the sorting flow channel. When the cell is identified as the target cell, the electromagnetic gas inlet valve is controlled to pump a gas into the gas inlet flow channel. When the target cell moves to the sorting region, the gas in the gas inlet flow channel may just move to the sorting region and blow the target cell into the target flow channel. When the cell is identified as the non-target cell, the electromagnetic gas inlet valve does not pump the gas into the gas inlet flow channel, and after the non-target cell moves to the sorting region, it continues to flow into the non-target flow channel with the cell suspension.

In this solution, the target flow channel, the non-target flow channel and the gas inlet flow channel are set to intersect with the sorting flow channel, and the distance d between the intersection of the axis of the gas inlet flow channel and the axis of the sorting flow channel and the intersection of the sorting flow channel, the target flow channel and the non-target flow channel is from 0.02 mm to 0.05 mm, so that the length of the sorting region is increased so as to extend the residence time of the target cells in the sorting region, and thus there are more suitable opportunities to pump the gas into the gas flow channel so as to blow the target cells into the target flow channel, thereby increasing the accuracy of target cell sorting.

After the gas in the gas inlet flow channel enters the sorting region, the gas exerts a deflecting force perpendicular to the original path of the cell on the cell. After the target cell receives the deflecting force provided by the gas, the moving path of the target cell is changed into a parabola path moving to the target cell flow channel. The shape of the parabola depends on the original flow velocity of the cell and the pressure of the inlet gas, and the included angle between two asymptotes of the parabola is the included angle between the sorting flow channel and the target flow channel. As the target cell moves in the sorting region, it is necessary to ensure that the target cell can enter the target cell flow channel and the moving direction of the target cell is parallel with the axis of the target flow channel when the moving distance of the target cell along the axis of the sorting flow channel is d; and when the distance d is from 0.02 mm to 0.05 mm and the included angle between the target flow channel and the sorting flow channel is from 100° to 130°, the target cell can smoothly enter the target cell flow channel and the moving direction of the target cell is parallel to the axis of the target cell flow channel. Besides, since the deflecting force required to change the path of the target cell when the included angle between the target flow channel and the sorting flow channel is from 100° to 130° is less than the deflecting force required to change the path of the target cell when the target flow channel is perpendicular to the sorting flow channel. Even if the pressure of the inlet gas in the present application is less than the pressure of the inlet gas in the prior art, the microfluidic chip of the present application can still complete cell sorting. A lower pressure of the inlet gas causes less damage to the target cell, so the microfluidic chip of the present application can cause less damage to the target cell than the prior art. Moreover, when the included angle between the non-target flow channel and the sorting flow channel is from 100° to 140°, after the target cell receives the deflecting force provided by the gas in the gas inlet flow channel, the included angle between the moving direction of the target cell and the axis of the non-target flow channel is larger, which further prevents the target cell from entering the non-target flow channel.

Preferably, the sorting flow channel includes a first flow channel and a second flow channel. A diameter of the first flow channel is from 0.1 mm to 0.12 mm. A diameter of the second flow channel is from 0.18 mm to 0.2 mm. The first flow channel communicates with the sample flow channel, and the second flow channel communicates with the target flow channel, the non-target flow channel and the gas inlet flow channel. The diameter of the second flow channel is greater than the diameter of the first flow channel, so that the movement velocity of the cells in the second flow channel can be reduced, and the gas flow in the gas inlet flow channel can be prevented from moving to the first flow channel. When part of the gas flow moves towards the first flow channel, this part of the gas flow cannot rush through a connecting end of the second flow channel and the first flow channel, which can prevent this part of the gas flow from flowing backwards and impacting the cells, causing damage to the cells.

Preferably, an end of the second flow channel connected with the first flow channel is tapered. The joint between the first flow channel and the second flow channel is tapered, so that the sample solution in the first flow channel can gently enter and fill the second flow channel.

Preferably, arc chamfers are respectively arranged between the second flow channel and the gas inlet flow channel, between the gas inlet flow channel and the non-target flow channel, between the non-target flow channel and the target flow channel, and between the target flow channel and the second flow channel. The arc chamfer between the second flow channel and the gas inlet flow channel is a first chamfer. The arc chamfer between the gas inlet flow channel and the non-target flow channel is a second chamfer. The arc chamfer between the non-target flow channel and the target flow channel is a third chamfer. The arc chamfer between the target flow channel and the second flow channel is a fourth chamfer. A radius of the first chamfer is from 0.08 mm to 0.1 mm. A radius of the second chamfer is from 0.08 mm to 0.1 mm. A radius of the third chamfer is from 0.12 mm to 0.15 mm. A radius of the fourth chamfer is from 0.18 mm to 0.2 mm. The intersections on side walls where the second flow channel, the gas inlet flow channel, the non-target flow channel and the target flow channel intersect are provided with the arc chamfers, and the arc of the chamfers coincides with the parabolic moving path of the cell, so that the movement of the cell can be guided. Even when the cell abuts against the side wall, the arc chamfer at the intersection on the side wall will not damage the cell. The experimental results show that when the radius of the first chamfer is from 0.08 mm to 0.1 mm, the radius of the second chamfer is from 0.08 mm to 0.1 mm, the radius of the third chamfer is from 0.12 mm to 0.15 mm and the radius of the fourth chamfer is from 0.18 mm to 0.2 mm, the chamfers have the best guiding effects on the cell.

Preferably, the sample flow channel includes a cell flow channel and a sheath fluid flow channel, and the sample region includes a mixed cell region and a sheath fluid region. The cell flow channel communicates with the mixed cell region, and the sheath fluid flow channel communicates with the sheath fluid region. The sheath fluid flow channel and the cell flow channel intersect at the liquid inlet end of the sorting flow channel. There are two sheath fluid flow channels. The two sheath fluid flow channels are respectively located on either side of the cell flow channel opposite to each other and arranged symmetrically about an axis of the cell flow channel. A diameter of the sheath fluid flow channel is the same as a diameter of the cell flow channel, and a diameter of the non-target flow channel is twice a diameter of the target flow channel. The sheath fluid may wrap the cells such that the cells flow into the detection area of the cytometer in a straight single line. The two sheath fluid flow channels are respectively located on either side of the cell flow channel, so that the cells flowing into the sorting flow channel are located in the middle of the sorting flow channel. The diameter of the sheath fluid flow channel is the same as the diameter of the cell flow channel, and the diameter of the non-target flow channel is twice the diameter of the target flow channel, so that a ratio of the cell suspension entering the sorting flow channel to the sheath fluids on the two sides is 1:1:1. When the liquid in the sorting flow channel is not subject to the external disturbance, the sheath fluid on the side close to the target flow channel flows into the target flow channel, and the cell suspension and the sheath fluid on the other side flow into the non-target flow channel, thereby automatically guiding the non-target cells into the non-target flow channel.

Preferably, a length of the target flow channel is not greater than 5 mm. The pressure of the gas pumped into the gas inlet flow channel should not be too high, otherwise the gas entering the microfluidic chip will interfere in the whole flow channel. Thus, thrust of the gas on the target cell is insufficient to make the target cell move a very long distance in the target flow channel. If the target flow channel is too long, the target cell will stay in the target flow channel and cannot reach the target cell pool. As a result, the length of the target flow channel cannot be too large. The experimental results show that when the length of the target flow channel is not greater than 5 mm, the thrust of the gas on the target cell can make the target cell smoothly pass through the target flow channel and enter the target cell pool.

Preferably, an included angle between the sheath fluid flow channel and the cell flow channel is from 25° to 35°. The sheath fluid flow channels are each provided with a serpentine flow resistance section for reducing a flow velocity of a sheath fluid in the sheath fluid flow channel. As the included angle between the sheath fluid flow channel and the cell flow channel increases, the impact of the flow of sheath fluid on the flow of cell suspension after the sheath fluid converges with the cell suspension becomes larger, thus impacting the cells in the flow of cell suspension. The experimental results show that when the included angle between the sheath fluid flow channel and the cell flow channel is from 25° to 35°, the sheath fluid can be smoothly mixed with the cell suspension. The flow resistance is serpentine. After the sheath fluid passes through the serpentine sheath fluid flow channel, the kinetic energy of the sheath fluid is reduced, and the flow velocity of the sheath fluid is reduced, thereby reducing the flow velocity of the sample solution entering the first flow channel and the moving speed of the cells.

Compared with the prior art, the present invention has the following beneficial effects: The microfluidic chip in this solution does not cause damage to the cells during cell sorting. In this solution, the cell sorting region is expanded so as to extend the residence time of the target cells in the cell sorting region, so that there are more suitable opportunities to pump the gas, thereby preventing the target cells from entering the non-target cell pool due to the slow pumping of gas, and increasing the accuracy of cell sorting. Moreover, the target cells can be pushed into the target flow channel by using the gas with a lower pressure. The sorting flow channel can reduce the moving speed of the cells and prevent the gas from flowing backwards, which can further increase the accuracy of cell sorting and avoid damage to the cells. The intersections on the side walls where the second flow channel, the gas inlet flow channel, the non-target flow channel and the target flow channel intersect are provided with the arc chamfers, so that the cells entering the sorting region can be guided.

DETAILED DESCRIPTION

Figure 1:
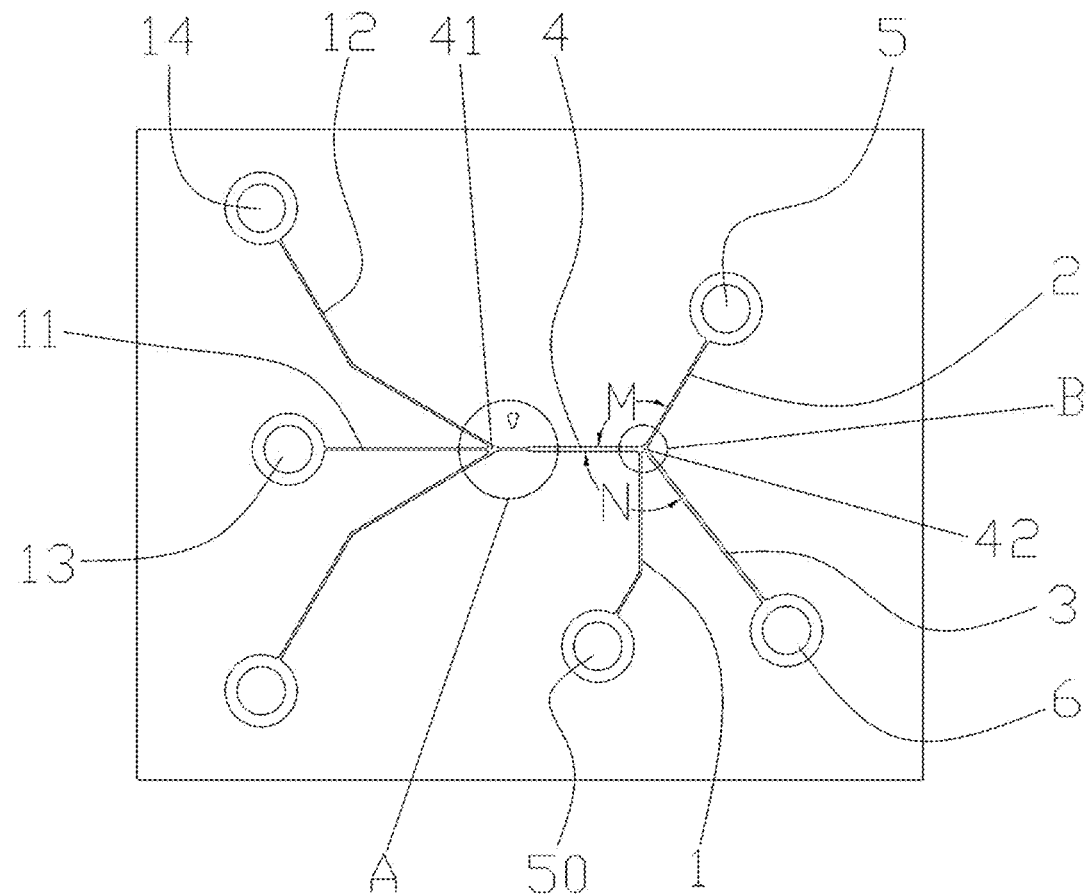
FIG. 1 is a schematic structural view of a microfluidic chip for sorting living cells according to the present invention.

The attached drawings are only for illustrative purposes, and cannot be understood as a limitation of the present invention. In order to better illustrate this embodiment, some components in the accompanying drawings are omitted, enlarged or reduced, and do not represent the dimensions of the actual component. It can be understood for those skilled in the art that some well-known structures in the accompanying drawings and descriptions thereof may be omitted. The positional relationships described in the accompanying drawings are for exemplary illustration only and are not to be understood as a limitation of the present invention.

The same or similar reference numerals in the accompanying drawings of the embodiment of the present invention correspond to the same or similar components. In the description of the present invention, it should be understood that if the orientation or positional relationship indicated by the terms "up", "down", "left", "right", "long" and "short" is based on the orientation or positional relationship shown in the accompanying drawings, it is only for the convenience of describing the present invention and simplifying the description, and does not indicate or imply that the device or element referred to must have a specific orientation, or be constructed and operated in a specific orientation. Therefore, the terms describing the positional relationship in the accompanying drawings are only used for illustrative purposes, and are not to be construed as limiting the present invention. For those of ordinary skill in the art, the specific meaning of the above terms may be understood according to specific situations.

The technical solution of the present invention will be further described in detail through the specific embodiments in conjunction with the accompanying drawings.

Embodiment 1

Figure 2:
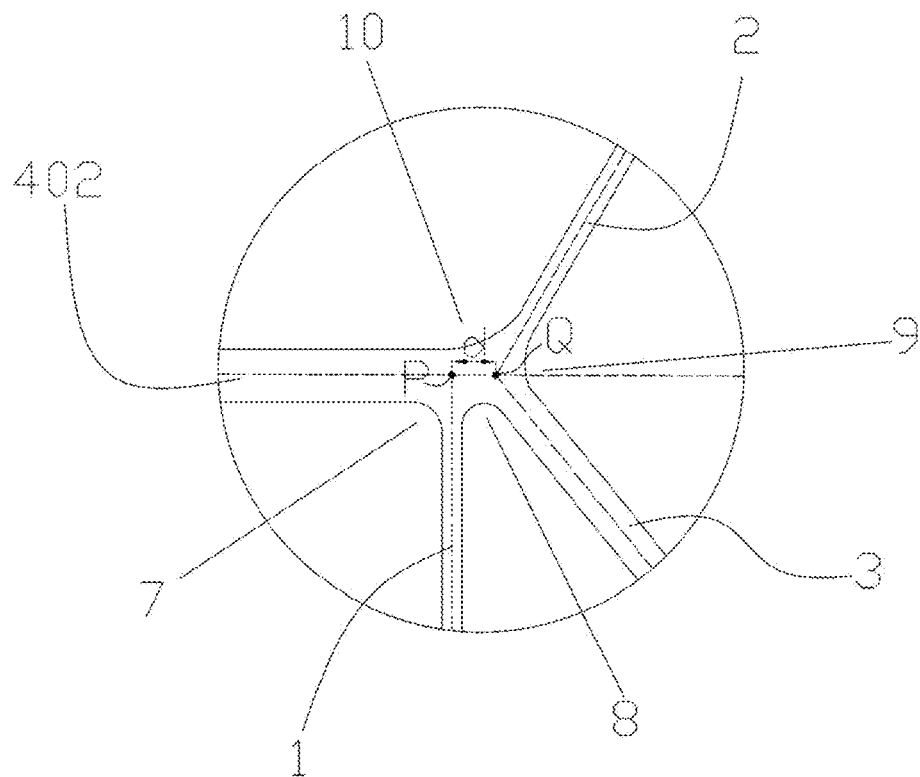
FIG. 2 is an enlarged view of B in FIG. 1 according to the microfluidic chip for sorting living cells of the present invention.

As shown in FIG. 1 and FIG. 2, a microfluidic chip for sorting living cells in Embodiment 1 includes a sample region, a sample flow channel communicating with the sample region, an electromagnetic gas inlet valve 50, a gas inlet flow channel 1 communicating with the electromagnetic gas inlet valve 50, a target cell pool 5, a target flow channel 2 communicating with the target cell pool 5, a non-target cell pool 6, a non-target flow channel 3 communicating with the non-target cell pool 6, and a sorting flow channel 4 for cell sorting. The sample flow channel communicates with a liquid inlet end 41 of the sorting flow channel 4, the target flow channel 2 and the non-target flow channel 3 communicate with a liquid outlet end 42 of the sorting flow channel 4, and the gas inlet flow channel 1 communicates with the sorting flow channel 4 and is located on the sorting flow channel 4 close to the liquid outlet end 42. The gas inlet flow channel 1 and the non-target flow channel 3 are located on one side of the sorting flow channel 4, and the target flow channel 2 is located on the other side of the sorting flow channel 4. An included angle M between the target flow channel 2 and the sorting flow channel 4 is 120°. An included angle N between the non-target flow channel 3 and the sorting flow channel 4 is 128°. An axis of the gas inlet flow channel 1 is perpendicular to an axis of the sorting flow channel 4. A distance d between an intersection P of the axis of the gas inlet flow channel 1 and the axis of the sorting flow channel 4 and an intersection Q of the sorting flow channel 4, the target flow channel 2 and the non-target flow channel 3 is 0.05 mm. The sorting region is at an end of the sorting flow channel 4 that intersects with the target flow channel 2, the non-target flow channel 3 and the gas inlet flow channel 1.

Working principle or working process of this embodiment: When the microfluidic chip is running, target cells and non-target cells in the sample region enter the sample flow channel with the flow of a cell suspension and are arranged individually and linearly in the sample flow channel. As the cell suspension continuously flows forward, the target cells and the non-target cells pass through the sorting flow channel 4 and then enter the sorting region. A device for identifying cell target signals identifies cells entering the sorting flow channel 4. When the cell is identified as the target cell, the electromagnetic gas inlet valve 50 is controlled to pump a gas into the gas inlet flow channel 1. When the target cell moves to the sorting region at the tail end of the sorting flow channel 4, the gas in the gas inlet flow channel 1 may just move to the sorting region and blow the target cell into the target flow channel 2. When the cell is identified as the non-target cell, the electromagnetic gas inlet valve 50 does not pump the gas into the gas inlet flow channel 1, and after the non-target cell moves to the sorting region at the tail end of the sorting flow channel 4, it continues to flow into the non-target flow channel 3 with the cell suspension.

TABLE 1

Control experiment of microfluidic chips

| | Control group 1 | Control group 2 | Present application 1 | Present application 2 |
|---|---|---|---|---|
| Target cells | Fluor-488 labeled cells | Fluor-488 labeled cells | Fluor-488 labeled cells | Fluor-488 labeled cells |
| Total number of cells to be tested | 50000 | 50000 | 50000 | 100000 |
| Total number of target cells | 8030 | 38500 | 10000 | 5000 |
| Flow velocity of sheath fluid (mm/s) | 120 | 120 | 120 | 120 |
| Pressure of gas (mbar) | 20 | 30 | 20 | 30 |
| Duration of experiment (min) | 103 | 183 | 128 | 96 |
| Total target cells obtained | 67 | 1562 | 6487 | 3821 |
| Accuracy | 0.83% | 4.05% | 81.24% | 76.42% |

The cell sorting chip used in the control groups is the microfluidic chip for simultaneously detecting multiple fluorescence signals in cells in the prior art, and the microfluidic chip used in the present application is the microfluidic chip described in this solution. As can be seen, by comparing control group 1 and control group 2 with the present application 1 and the present application 2, in the case of the same type of target cells and the same pressure of inlet gas and flow velocity of cells, the accuracy of cell sorting in the present application is much greater than that in the control groups. By comparing control group 1 with control group 2, in the case of constant flow velocity of cells, the greater the pressure of the inlet gas, the higher the accuracy of cell sorting. However, as can be seen from the comparison of control group 1 and control group 2 with the present application 1 and the present application 2, when the pressures in the two groups are reduced equally, the fluctuation in the accuracy of cell sorting is greater in the control group than in the present application. As can be seen from the above experimental data, after the cell sorting region is expanded and the included angle between the target flow channel and the sorting flow channel is adjusted, the accuracy of cell sorting can be significantly increased; and when a lower pressure of gas is used to drive the target cells to deflect, the fluctuation in the pressure of gas has little influence on the accuracy of cell sorting, and the cells can still be sorted effectively.

Beneficial effects of this embodiment: In this solution, the cell sorting region is expanded so as to extend the residence time of the target cells in the cell sorting region, so that there are more suitable opportunities to pump the gas, thereby preventing the target cells from entering the non-target cell pool due to the slow pumping of gas, and increasing the accuracy of cell sorting. Moreover, when the cells are driven to deflect, the target cells can be pushed into the target flow channel by using the gas with a lower pressure. The lower the pressure of gas, the less the damage to the target cells caused by the gas flow, and the higher the activity of the target cells that can be obtained.

Embodiment 2

Figure 3:
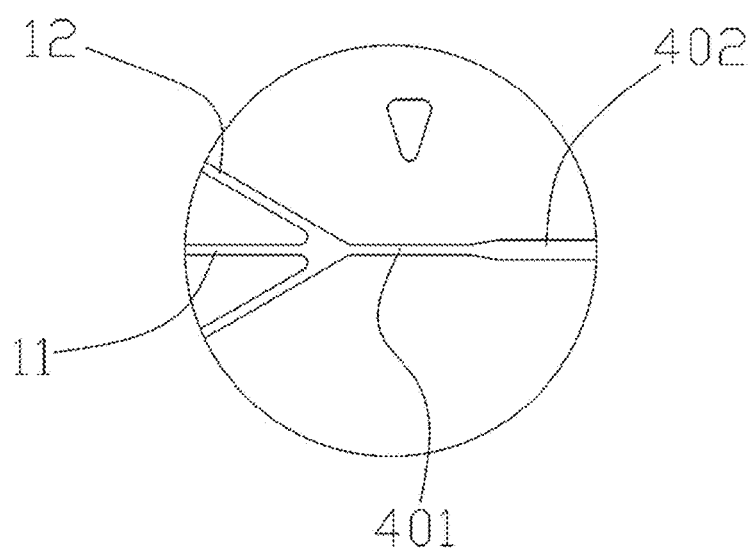
FIG. 3 is an enlarged view of A in FIG. 1 according to the microfluidic chip for sorting living cells of the present invention.

In a microfluidic chip for sorting living cells in Embodiment 2, as shown in FIG. 1 to FIG. 3, the structures of the sorting flow channel 4 and the sorting region are further limited on the basis of Embodiment 1.

Specifically, the sorting flow channel 4 includes a first flow channel 401 and a second flow channel 402. A diameter of the first flow channel 401 is 0.1 mm. A diameter of the second flow channel 402 is 0.2 mm. The first flow channel 401 communicates with the sample flow channel, and the second flow channel 402 communicates with the target flow channel 2, the non-target flow channel 3 and the gas inlet flow channel 1.

Specifically, an end of the second flow channel 402 connected with the first flow channel 401 is tapered.

Specifically, arc chamfers are respectively arranged between the second flow channel 402 and the gas inlet flow channel 1, between the gas inlet flow channel 1 and the non-target flow channel 3, between the non-target flow channel 3 and the target flow channel 2, and between the target flow channel 2 and the second flow channel 402. The arc chamfer between the second flow channel 402 and the gas inlet flow channel 1 is a first chamfer 7. The arc chamfer between the gas inlet flow channel 1 and the non-target flow channel 3 is a second chamfer 8. The arc chamfer between the non-target flow channel 3 and the target flow channel 2 is a third chamfer 9. The arc chamfer between the target flow channel 2 and the second flow channel 402 is a fourth chamfer 10. A radius of the first chamfer 7 is 0.1 mm. A radius of the second chamfer 8 is 0.1 mm. A radius of the third chamfer 9 is 0.15 mm. A radius of the fourth chamfer 10 is 0.2 mm.

Beneficial effects of this embodiment: The diameter of the second flow channel 402 is greater than the diameter of the first flow channel 401, so that the moving velocity of the cells in the second flow channel 402 can be reduced, and the gas flow in the gas inlet flow channel 1 can be prevented from moving to the first flow channel 401. When part of the gas flow moves towards the first flow channel 401, this part of the gas flow cannot rush through the connecting ends of the second flow channel 402 and the first flow channel 401, which can prevent this part of the gas flow from flowing backwards, impacting the cells, and causing damage to the cells. The joint between the first flow channel 401 and the second flow channel 402 is tapered, so that the sample solution in the first flow channel 401 can gently enter and fill the second flow channel 402. The intersections on side walls where the second flow channel 402, the gas inlet flow channel 1, the non-target flow channel 3 and the target flow channel 2 intersect are provided with the arc chamfers, and the shapes of the arc chamfers coincide with the parabolic moving path of the cell, so that the cell flowing into the sorting region can be guided, making it easier for the non-target cells to flow into the non-target flow channel 3 and the target cells to flow into the target flow channel 2.

Embodiment 3

In a microfluidic chip for sorting living cells in Embodiment 3, as shown in FIG. 1 to FIG. 3, the structures of the sample flow channel, the target flow channel 2 and the non-target flow channel 3 are further limited on the basis of Embodiment 1 or Embodiment 2.

Specifically, the sample flow channel includes a cell flow channel 11 and sheath fluid flow channels 12, and the sample region includes a mixed cell region 13 and a sheath fluid region 14. The cell flow channel 11 communicates with the mixed cell region 13, and the sheath fluid flow channels 12 communicate with the sheath fluid region 14. The sheath fluid flow channels 12 and the cell flow channel 11 intersect at the liquid inlet end 41 of the sorting flow channel 4. There are two sheath fluid flow channels 12. The two sheath fluid flow channels 12 are respectively located on either side of the cell flow channel 11 opposite to each other and arranged symmetrically about an axis of the cell flow channel 11. A diameter of the sheath fluid flow channel 12 is the same as a diameter of the cell flow channel 11, and a diameter of the non-target flow channel 3 is twice a diameter of the target flow channel 2.

Specifically, a length of the target flow channel 2 is 4 mm. An included angle between the sheath fluid flow channel 12 and the cell flow channel 11 is 25°. The sheath fluid flow channels 12 are each provided with a serpentine flow resistance section (not shown) for reducing a flow velocity of a sheath fluid in the sheath fluid flow channel 12.

Beneficial effects of this embodiment: The diameter of the sheath fluid flow channel 12 is the same as the diameter of the cell flow channel 11, and the diameter of the non-target flow channel 3 is twice the diameter of the target flow channel 2, so that the ratio of the cell suspension entering the sorting flow channel 4 to the sheath fluids on the two sides is 1:1:1. When the liquid in the sorting flow channel 4 is not subject to the external disturbance, the sheath fluid on the side close to the target flow channel 2 flows into the target flow channel 2, and the cell suspension and the sheath fluid on the other side flow into the non-target flow channel 3, thereby automatically guiding the non-target cells into the non-target flow channel 3. When the length of the target flow channel 2 is 4 mm, thrust of the gas on the target cell can make the target cell smoothly pass through the target flow channel 2 and enter the target cell pool 5. As the included angle between the sheath fluid flow channel 12 and the cell flow channel 11 increases, the impact of the flow of sheath fluid on the flow of cell suspension after the sheath fluid converges with the cell suspension becomes larger, thus impacting the cells in the flow of cell suspension. The experimental results show that when the included angle between the sheath fluid flow channel 12 and the cell flow channel 11 is 25°, the sheath fluid can be smoothly mixed with the cell suspension. The flow resistance is serpentine. After the sheath fluid passes through the serpentine sheath fluid flow channel 12, the kinetic energy of the sheath fluid is reduced, and the flow velocity of the sheath fluid is reduced, thereby reducing the flow velocity of the sample solution entering the first flow channel 401 and the moving speed of the cells.

Apparently, the above embodiments of the present invention are merely examples for clearly explaining the present invention, and are not limitations to the implementations of the present invention. For those of ordinary skill in the art, other variations or modifications in different forms can be made based on the above description. There is no need and no way to exhaust all of the implementations here. Any modification, equivalent substitution, or improvement made within the spirit and principle of the present invention shall fall into the protection scope of the claims of the present invention.

What is claimed is:

1. A microfluidic chip for sorting living cells, comprising: a mixed cell region, a sheath fluid region, a cell flow channel communicating with the mixed cell region, a sheath fluid flow channel communicating with the sheath fluid region, an electromagnetic gas inlet valve, a gas inlet flow channel communicating with the electromagnetic gas inlet valve, a target cell pool, a target flow channel communicating with the target cell pool, a non-target cell pool, a non-target flow channel communicating with the non-target cell pool, and a sorting flow channel;

the cell flow channel and the sheath fluid flow channel communicate with a liquid inlet end of the sorting flow channel, the target flow channel and the non-target flow channel communicate with a liquid outlet end of the sorting flow channel, the gas inlet flow channel communicates with the sorting flow channel and is located on the sorting flow channel close to the liquid outlet end of the sorting flow channel, the target flow channel is located on one side of the sorting flow channel, the gas inlet flow channel and the non-target flow channel are located on the other side of the sorting flow channel, an included angle between the target flow channel and the sorting flow channel is from 100° to 130°, an included angle between the non-target flow channel and the sorting flow channel is from 100° to 140°, and an axis of the gas inlet flow channel is perpendicular to an axis of the sorting flow channel; and a distance between an intersection of the axis of the gas inlet flow channel and the axis of the sorting flow channel and an intersection of the axis of the sorting flow channel, an axis of the target flow channel and an axis of the non-target flow channel is from 0.02 mm to 0.05 mm.

2. The microfluidic chip for sorting living cells according to claim 1, wherein the sorting flow channel comprises a first flow channel and a second flow channel, wherein a diameter of the first flow channel is from 0.1 mm to 0.12 mm; and a diameter of the second flow channel is from 0.18 mm to 0.2 mm, the first flow channel communicates with the cell flow channel and the sheath fluid flow channel, and the second flow channel communicates with the target flow channel, the non-target flow channel and the gas inlet flow channel.

3. The microfluidic chip for sorting living cells according to claim 2, wherein an end of the second flow channel connected with the first flow channel is tapered.

4. The microfluidic chip for sorting living cells according to claim 2, wherein arc chamfers are respectively arranged between a side wall of the second flow channel and a side wall of the gas inlet flow channel, between the side wall of the gas inlet flow channel and a side wall of the non-target flow channel, between the side wall of the non-target flow channel and a side wall of the target flow channel, and between the side wall of the target flow channel and the side wall of the second flow channel; wherein the arc chamfer between the side wall of the second flow channel and the side wall of the gas inlet flow channel is a first chamfer; the arc chamfer between the side wall of the gas inlet flow channel and the side wall of the non-target flow channel is a second chamfer; the arc chamfer between the side wall of the non-target flow channel and the side wall of the target flow channel is a third chamfer; and the arc chamfer between the side wall of the target flow channel and the side wall of the second flow channel is a fourth chamfer.

5. The microfluidic chip for sorting living cells according to claim 4, wherein a radius of the first chamfer is from 0.08 mm to 0.1 mm; a radius of the second chamfer is from 0.08 mm to 0.1 mm; a radius of the third chamfer is from 0.12 mm to 0.15 mm; and a radius of the fourth chamfer is from 0.18 mm to 0.2 mm.

6. The microfluidic chip for sorting living cells according to claim 1, wherein the sheath fluid flow channel and the cell flow channel intersect at the liquid inlet end of the sorting flow channel.

7. The microfluidic chip for sorting living cells according to claim 1, wherein there are two sheath fluid flow channels; the two sheath fluid flow channels are respectively located on either side of the cell flow channel opposite to each other and arranged symmetrically about an axis of the cell flow channel; and a diameter of the sheath fluid flow channel is the same as a diameter of the cell flow channel, and a diameter of the non-target flow channel is twice a diameter of the target flow channel.

8. The microfluidic chip for sorting living cells according to claim 7, wherein a length of the target flow channel is not greater than 5 mm.

9. The microfluidic chip for sorting living cells according to claim 7, wherein an included angle between the sheath fluid flow channel and the cell flow channel is from 25° to 35°.

10. The microfluidic chip for sorting living cells according to claim 9, wherein the sheath fluid flow channels are each provided with a serpentine flow resistance section for reducing a flow velocity of a sheath fluid in the sheath fluid flow channel.

* * * * *